United States Patent
Zuppiger et al.

(10) Patent No.: US 7,964,160 B2
(45) Date of Patent: Jun. 21, 2011

(54) PIPETTING APPARATUS WITH A COMPUTER PROGRAM PRODUCT AND A METHOD FOR ACCEPTING OR REJECTING PIPETTED LIQUID SAMPLES

(75) Inventors: Adi Zuppiger, Siebnen (CH); Pascal Stäheli, Zollikerberg (CH); Joas Leemann, Ottikon (CH); Carsten Hase, Zürich (CH)

(73) Assignee: Tecan Trading AG, Mannedorf (CH)

( * ) Notice: Subject to any disclaimer, the term of this patent is extended or adjusted under 35 U.S.C. 154(b) by 1008 days.

(21) Appl. No.: 11/459,073

(22) Filed: Jul. 21, 2006

(65) Prior Publication Data
US 2007/0025882 A1  Feb. 1, 2007

(30) Foreign Application Priority Data

Jul. 22, 2005  (CH) .................................. 1223/05
Jun. 30, 2006  (DE) .................... 20 2006 010 293 U

(51) Int. Cl.
*B01L 3/00* (2006.01)
(52) U.S. Cl. ........ 422/500; 422/501; 422/502; 422/503; 436/180; 73/864.11
(58) Field of Classification Search ............ 422/99–100, 422/500–503; 436/180; 73/864.11
See application file for complete search history.

(56) References Cited

U.S. PATENT DOCUMENTS

| | | | |
|---|---|---|---|
| 4,340,390 A | 7/1982 | Collins et al. |
| 4,675,301 A | 6/1987 | Charneski et al. |
| 4,794,085 A | 12/1988 | Jessop et al. |
| 5,638,986 A | 6/1997 | Tuominen et al. |
| 6,179,584 B1 | 1/2001 | Howitz et al. |
| 6,813,944 B2 | 11/2004 | Mayer et al. |
| 6,898,981 B1 | 5/2005 | Boillat et al. |
| 6,938,504 B2 | 9/2005 | Camenisch |

FOREIGN PATENT DOCUMENTS

| | | |
|---|---|---|
| CH | 695 166 A5 | 12/2005 |
| DE | 1 703 406 | 3/1972 |
| EP | 1 142 624 A1 | 3/1996 |
| EP | 1 207 396 A1 | 10/2000 |

*Primary Examiner* — Jyoti Nagpaul
(74) *Attorney, Agent, or Firm* — Notaro, Michalos & Zaccaria P.C.

(57) ABSTRACT

The invention relates to a pipetting apparatus (1) having a pipette tip (2) for aspirating and dispensing liquid samples; a pump (4) for generating negative pressure or positive pressure in the pipette tip (2) that is connected to the pipette tip (2) by means of a pump conduit (3); a fluid chamber (5) defined by the pipette tip (2) and/or the pump conduit (3); a measurement probe (6) functionally connected to the fluid chamber (5) for measuring the physical parameters resulting in this fluid chamber (5) during pipetting; and a device control system (7) with a processor (8), in which an activated computer program product enables the control system (7) of the pipetting apparatus (1) to individually accept or reject pipetted liquid samples on the basis of the physical parameters measured. The pipetting apparatus (1) in accordance with the invention is characterized in that it comprises a data storage device (9) for storing an actual measured curve (41) measured during pipetting and a simulated curve (42) for such a pipetting procedure and also a computer program product that in an activated state enables the processor (8) of this pipetting apparatus (1) to generate this simulated curve (42) and approximate it to the actual measured curve (41) iteratively to create an iterative curve (43) and then matching the pipetting and/or the corresponding pipetted liquid samples to one of a plurality of decision-making criteria on the basis of sections of the measured curve (44) in the actual measured curve (41) that deviate from defined threshold values (45) in relation to the corresponding sections of the curve (46) of the iterative curve (43). A corresponding computer program product and method are included within the scope of the invention.

10 Claims, 4 Drawing Sheets

US 7,964,160 B2

PIPETTING APPARATUS WITH A COMPUTER PROGRAM PRODUCT AND A METHOD FOR ACCEPTING OR REJECTING PIPETTED LIQUID SAMPLES

RELATED PATENT APPLICATIONS

This patent application claims the priority of the Swiss initial application No. CH 01223/05 filed on Jul. 22, 2005 and of the German utility model No. 20 2006 010 293.0 filed on Jun. 30, 2006. Express reference is made here to the content of these two priority applications and the content disclosed therein is incorporated herein for all purposes.

TECHNICAL FIELD OF THE INVENTION

The invention relates to a pipetting apparatus having a pipette tip for aspirating and dispensing liquid samples; a pump connected to the pipette tip by means of a pump conduit for generating negative pressure or positive pressure in the pipette tip; a fluid chamber defined by the pipette tip and/or the pump conduit; a measurement probe functionally connected to the fluid chamber for measuring the resultant physical parameters in this fluid chamber during pipetting and a device control system with a processor in which an activated computer program product enables the control system of the pipetting apparatus to individually accept or reject each of the pipetting actions and therefore also each of the pipetted liquid samples on the basis of the physical parameters measured. Moreover, the present invention relates to a pipetting apparatus with a corresponding computer program product and a method for accepting or rejecting pipetted liquid samples and pipette procedures.

In the technical field of liquid handling, in particular with respect to pipetting fluids, there has long been a need to evaluate pipetted samples on the basis of predetermined quality criteria. Primarily, in the case of the automatic pipetting of fluids in microplates with for instance 96, 384 or 1536 wells, it is advantageous to know the current addresses of the correctly prepared sample volumes, but above all also of those useless samples in each microplate. Also, when pipetting liquid samples from other containers, such as for instance troughs, test or sample tubes etc., a distinction needs to be made between the accepted pipetted samples and the rejected ones.

Only some of the known pumps for operating pipetting apparatus shall serve as examples here and these are in no way intended to be exhaustive.

KNOWN STATE OF THE ART

Document EP 1 207 396 A1 discloses an apparatus for dispensing liquid samples that includes a conduit allowing the flow of system liquid and a valve for closing this conduit at one end with a pipette tip at its other end. In addition, this known apparatus encompasses a measurement facility for recording the flow of the system liquid in this conduit, a means of control for generating a flow in this conduit in one or the other direction, and electronic means of evaluation that responds to data recorded by the measurement facility and exerts an effect on the valve, and the means of control so that a liquid sample is taken up by the pipette tip and then a specific sample quantity is dispensed.

U.S. Pat. No. 6,938,504 B2 makes known for instance a method for continuously monitoring the pressure in a disposable pipette tip during pipetting. The existing pressure characteristic is recorded and compared graphically or mathematically with the range of tolerance of a previously determined characteristic pressure curve. If the existing pressure characteristic falls within the range of tolerance, the sample is accepted. In addition to reaching direct conclusions regarding the success or failure of a pipetting process, this approach enables systematic errors to be identified. This method may be sufficient for constantly similar, homogenous samples, but it presents considerable difficulties when the samples to be pipetted display a large degree of heterogeneity. Such cases can for instance be observed with mass inspection of blood samples, the viscosity of which can range from 1 mPas to 6 mPas. If such variation must be included in the range of tolerance, the "acceptable range" is such that it is no longer suitable for ascertaining the existence of blood clots or air bubbles.

OBJECTS AND FEATURES OF THE INVENTION

One object of the present invention is to propose an alternative pipetting apparatus of the kind discussed above that is provided with a computer program product which enables the control system of the pipetting apparatus to individually accept or reject pipetted samples from varying liquid samples on the basis of the physical parameters measured.

A further object of the present invention is to propose a computer program product that enables the control system of the pipetting apparatus to individually accept or reject pipetted samples from varying liquid samples on the basis of the physical parameters measured.

Another object of the present invention is to propose a method that enables pipetting of varying liquid samples to be individually accepted or rejected on the basis of the physical parameters measured.

As cited initially the state of the art makes known not only pipetting apparatus with flow measurement, but also with pressure measurement for monitoring the process during pipetting. The present invention offers alternative solutions to both of these known methods of monitoring:

In accordance with a first aspect, a pipetting apparatus is proposed, comprising:
(a) a pipette tip for aspirating and dispensing liquid samples,
(b) a pump connected to the pipette tip by means of a pump conduit for generating negative pressure or positive pressure in the pipette tip;
(c) a fluid chamber defined by the pipette tip and/or the pump conduit;
(d) a measurement probe functionally connected to the fluid chamber for measuring the physical parameters resulting in this fluid chamber during pipetting; and
(e) a device control system with a processor, in which an activated computer program product enables the control system of the pipetting apparatus to individually accept or reject pipetted liquid samples on the basis of the physical parameters measured.

The pipetting apparatus in accordance with the invention is characterized in that it also comprises:
(f) a data storage device for storing an actual measured curve measured during pipetting and a simulated curve for such a pipetting procedure; and
(g) a computer program product that in an activated state enables the processor embodied in this pipetting apparatus to generate this simulated curve and to approximate it iteratively to the actual measured curve in order to create an iterative curve and then to match pipetting to one of a plurality of decision-making criteria, on the basis of sections of the measured curve within the actual measured curve that deviate from respective sections of the iterative curve in terms of defined threshold values.

In accordance with a second aspect, a computer program product is proposed to accept or reject pipetted liquid samples. In an activated state this computer program product enables a processor of a pipetting apparatus to generate a simulated curve for a pipetting procedure that essentially corresponds to the pressure characteristic curve or the flow pattern in this fluid chamber:

(a) on the basis of known variables entered into the processor that are preferably selected from a group comprising a set of parameters corresponding to a fluid class, a volume of fluid to be pipetted, and one type of pipette tip to be used;
(b) on the basis of typical pipetting parameters stored in the processor and characterizing the selected fluid class that are preferably selected from a group comprising the viscosity and the density of the sample fluid, where the exact magnitude of said pipetting parameters is unknown; and
(c) on the basis of typical, unknown pipetting parameters stored in the processor and independent of the sample fluid that are preferably selected from a group comprising the outlet diameter of the pipette tip and the wettability of the pipette tip.

The set of parameters corresponding to a fluid class that is preferably used by the computer program product in accordance with the invention consists of variables selected from a group comprising the type, the ramp parameters and the delivery parameters of the pump used, the use and the volume of an "air gap", the insertion and withdrawal speed of the pipette tip, the insertion depth of the pipette tip, and the acceleration and deceleration ramps of pipette tip movements. This set of parameters also comprises the control parameters for the diluter pump and the robot arm guiding the pipette.

In accordance with a third aspect, a method is proposed that simulates a curve by employing a physical model and taking practical know-how into account, approximating said curve to an actual measured curve, and then comparing said curve with this measured curve by:

using a mathematical model to calculate a simulated curve, taking all essential parameters into consideration;
approximating the simulated curve to the actual measured curve to obtain an iterative curve, with the modifiable parameters (such as e.g. sample viscosity, surface tension, sample fluid density, and pipette tip geometry) being varied systematically;
comparing the actual measured curve with the iterative curve, analyzing the elements specific to the measured curve (such as e.g. slopes, maximums, zero crossovers);
classifying each individual pipetted sample on the basis of this comparison of the measured curve with the iterative curve, with specific criteria, such as for instance the proportion of the deficient volume serving as the basis, and
matching this classification of a pipetted sample to the corresponding sample.

Additional preferred and inventive features result from the dependent claims involved in each case.

In the context of the present invention, "data storage devices" are considered to be hard disks and working memories, e.g. RAM (random access memory) of computers and processors, with RAM being the preferred data storage device.

BRIEF DESCRIPTION OF THE FIGURES

The pipette apparatus, computer program product and method in accordance with the invention are described in greater detail with reference to schematic drawings that show preferred embodiments and therefore do not restrict the scope of the present invention. The figure shows.

DETAILED DESCRIPTION OF THE INVENTION

Figure 1:
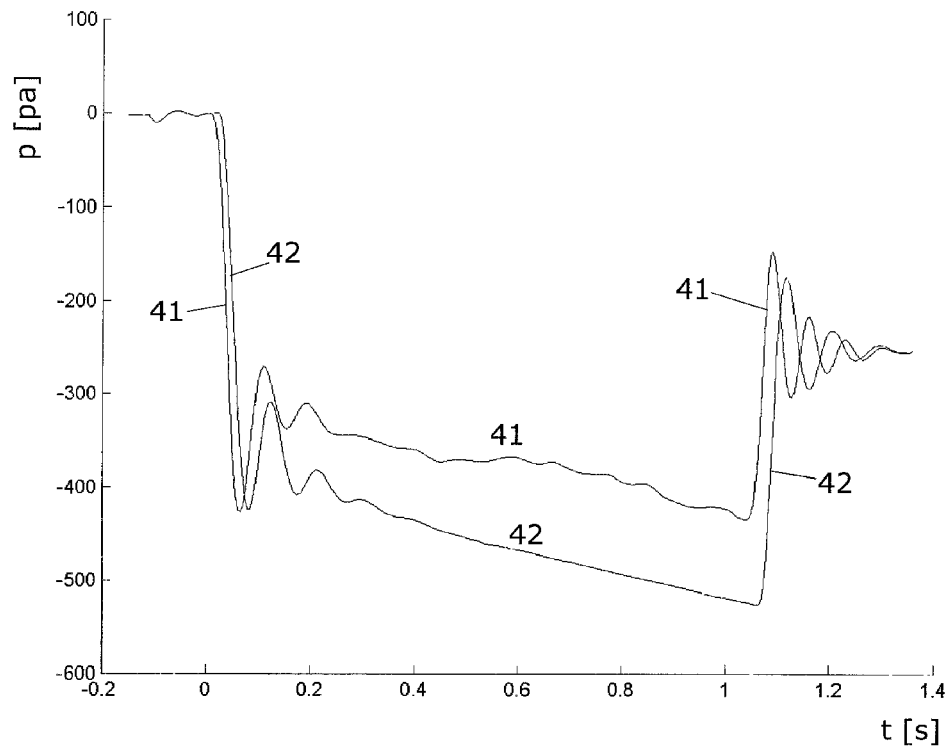
FIG. 1 Step 1, in which the sample density, the wetting contact angle and the presence of a system liquid have been taken into consideration.

The present invention will now be described in greater detail with reference to a selected example employing pressure measurement:

1. Generation of a Simulated Curve

The pipetting apparatus in accordance with the invention preferably comprises a modular configurable computer program product based on a combination of a physical model and characteristic curve parameter analysis. In accordance with one aspect of the invention, a pressure characteristic curve in a disposable pipette tip is simulated during fluid uptake (aspiration) and/or fluid output (dispensing), with a single pipette channel being modeled, preferably as a system having two or three non-linear interconnected, oscillating masses. Corresponding systems of differential equations have been proposed and numerical solutions determined. With respect to a pipetting apparatus equipped with a plunger pump, this involved a model incorporating the diluter with its plunger, the system liquid present as a liquid column in a fluid chamber of the pipette apparatus, and the sample fluid in the pipette tip. A large number of effects constitute significant parameters which characterize the selected fluid class, the exact magnitude of these parameters however, is unknown. These effects included for instance viscous attenuation, surface tension, the density and hydrostatic pressure of such a system liquid and a sample fluid, the geometry of a disposable pipette tip, the impact of a kinetic impulse on the sample, the resulting forces, and the pressure characteristic curve in the pipette tip. Other parameters have not been implemented as physical variables, but as parameters to be entered into the system, such as for instance the so-called fluid class, defined by a set of parameters, the sample volume to be pipetted, and the type of pipette tip used.

The fluid class consists of variables comprising the type of pump, pump dimensions, ramp parameters and delivery parameters of the pump used, the use and the volume of an "air gap" (cf. e.g. EP 1 207 396 A1, Paragraph 45), the insertion and withdrawal speed of the pipette tip, the insertion depth of the pipette tip, and the acceleration and deceleration ramps of pipette tip movements. Four such fluid classes have previously been defined for water, ethanol, dimethylsulfoxide (DMSO) and blood (serum/plasma) with the corresponding variables based on many years experience. The sample volume to be pipetted (for instance 25 µl) is entered as the "desired volume" and defines a target volume. The actual pipetted sample volume can be verified using other methods (photometry, gravimetric analysis).

The type of pipette tip to be used depends on the actual field of application, the type of sample and the number of volumes to be pipetted. If the risk of cross contamination with other samples has to be ruled out, it is preferable to use disposable pipette tips (normally of synthetic material). However, if large quantities of the same sample material is to be distributed in many sample units, it is preferable to use pipette needles (usually of steel).

In addition to these known variables to be entered into the processor or into the processor memory, there are other pipetting parameters that are also preferably stored in the processor that are dependent upon the selected class of fluid, the exact magnitude of which is however unknown. Such parameters are for instance the viscosity and the density of the sample fluid. In addition, further parameters such as for instance the ambient temperature and the air pressure can be taken into consideration.

It is also preferable to store parameters in the processor or processor memory that are independent of the sample fluid and also unknown. Such parameters include for instance the diameter of the outlet of the pipette tip and the wettability of the pipette tip.

In accordance with a preferred embodiment of the computer program product that can be activated in a pipetting apparatus, all these variables and parameters are used to generate a simulated curve for a pipetting process that corresponds principally to the pressure characteristic curve (or to the flow characteristic in an apparatus equipped with a flow meter) in this fluid chamber of the pipetting apparatus. Apparatus and methods for measuring a pressure characteristic curve in a pipetting apparatus have on the one hand been known for a long time (cf. e.g. U.S. Pat. Nos. 4,340,390; 4,675,301; 4,794,085) and on the other hand have recently been patented (cf. e.g. U.S. Pat. No. 6,938,504). Also known in the state of the art are apparatus and methods for the exact measurement of flow patterns in a conduit (cf. e.g. CH 695 166 A5; US 2003/0049877 A1 and U.S. Pat. No. 6,550,324 B1) and in particular in a pipetting apparatus (cf. e.g. U.S. Pat. No. 6,898,981 B1). Consideration of as many variables as possible serves to generate a meaningful simulated curve at the first attempt. The more parameters that are not taken into consideration during this phase, the longer it subsequently takes to fit the simulated curve to the actual measured curve.

In the context of the present invention, the term "fluid" refers to a liquid, a gas or a liquid gas mixture. Consequently, a "fluid chamber" or a "fluid filled chamber" contains a gas, a liquid and/or a gas liquid mixture or can contain one or several of these elements.

2. Fitting the Simulated Curve

Due to the physical nature of the model parameters that require adjusting or fitting, meaningful ranges of tolerance can be defined within which these parameters can vary. Fitting is performed for aspiration and dispensing independently. Eight parameters have been selected for aspiration and four parameters for dispensing. In order to minimize the time required for fitting, in this example several variables were extracted from the measured curve initially in order to find the most suitable starting point for fitting. Based on this starting point, the parameters for aspiration were fitted step by step, as shown in FIGS. 1 to 5.

In FIG. 1 the starting signals of the measured curve 41 and the simulated curve 42 are at the same level and their average defines the zero point of pressure after an initial approximation step that takes the sample density, the wetting contact angle and the presence of system liquid into consideration. Despite the very similar characteristics for these two curves, there is a clear disparity between the two steep falling flanks (left), the gently sloping plateaus (center), and the steep rising flanks (right). However, the signals at the end of both characteristic curves are very similar.

Figure 2:
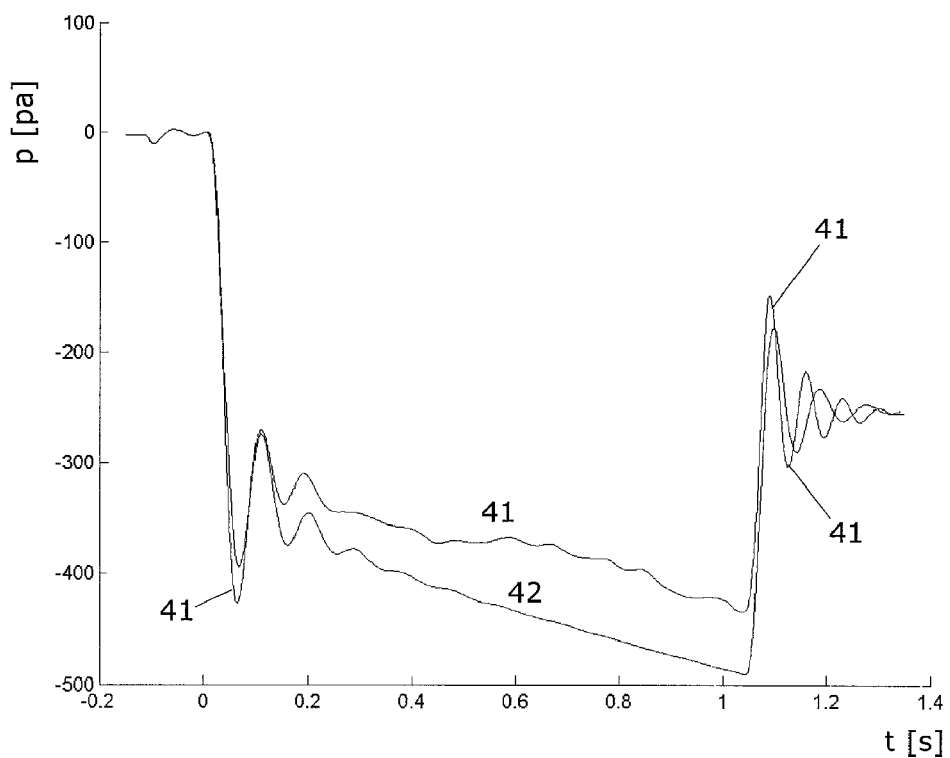
FIG. 2 Step 2, in which the aspiration rate and the radius of the pipette tip have been taken into consideration.

In FIG. 2 the two steep falling flanks (left) for the measured curve 41 and the simulated curve 42 lie practically on top of one another after a second approximation step that takes the aspiration rate and the radius of the pipette tip into consideration. The two gently inclined plateaus (center) and also the two steep rising flanks (right) are a little closer, but are still distinctly separated.

Figure 3:
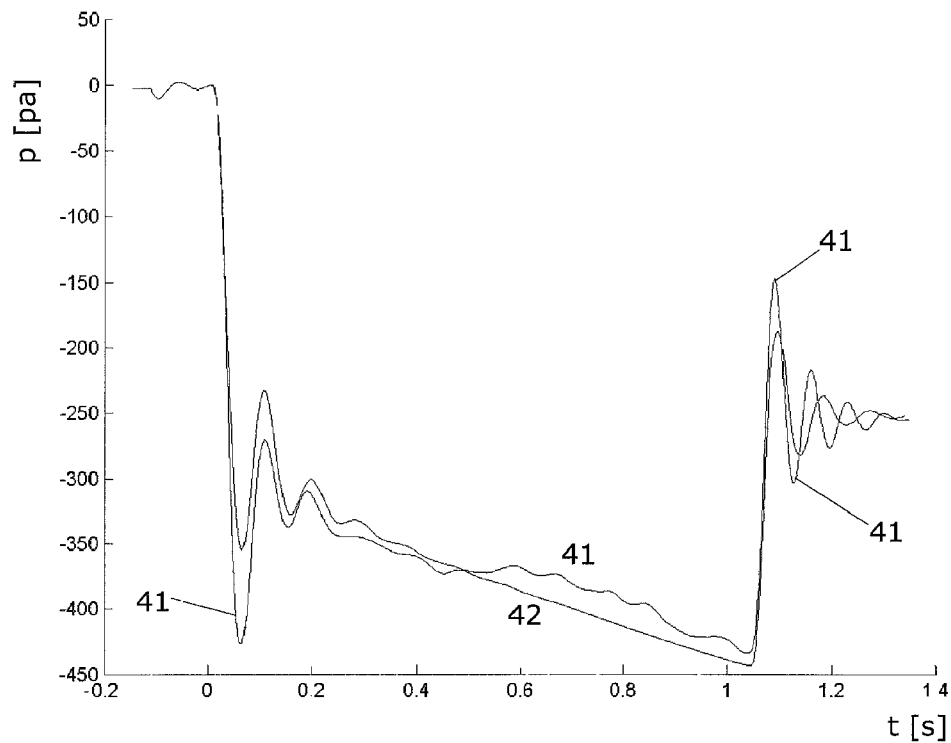
FIG. 3 Step 3, in which the viscosity of the sample has been taken into consideration.

In FIG. 3 the two steep falling flanks (left) are practically on top of one another after a third approximation step that takes the viscosity of the sample into consideration. The two slightly inclined plateaus (center) for the measured curve 41 and the simulated curve 42 are still closer and are partially overlapping. The two rapidly rising flanks (right) now lie practically on top of one another. However, the distinct differences at the tune point to the gently sloping plateaus are clearly apparent.

Figure 4:
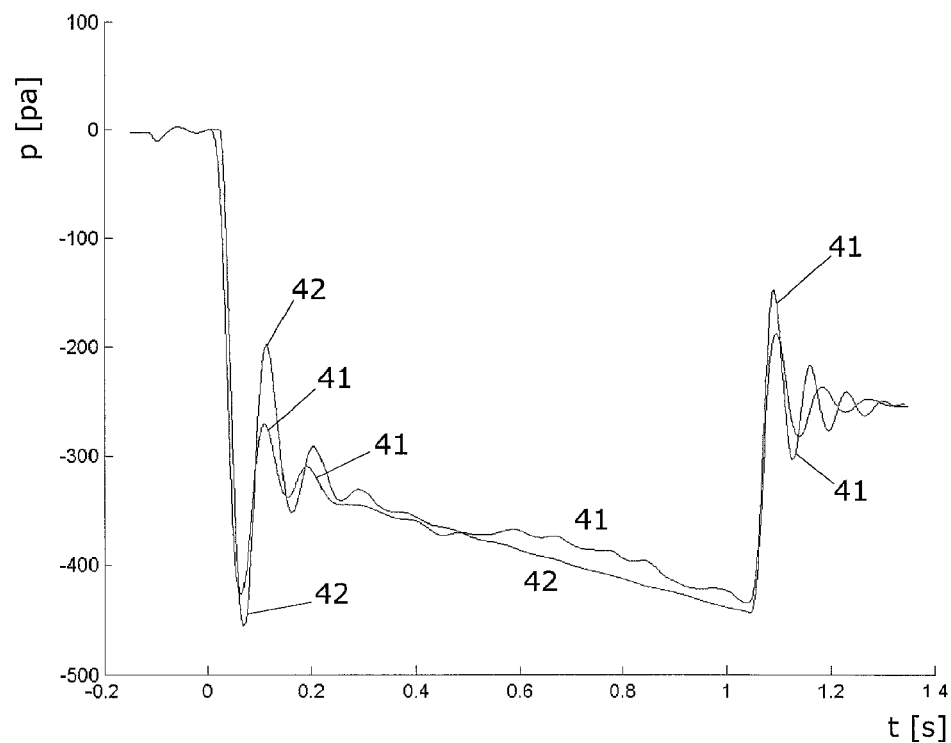
FIG. 4 Step 4, in which the static (diluter/plunger) friction has been taken into consideration.

In FIG. 4 the two steep falling flanks (left) are slightly apart again after a fourth approximation step that takes the static (diluter/plunger) friction into consideration. The two gently inclined plateaus (center) are now very close and are partially overlapping. In particular, the values before the rise of the right-hand flank now lie very close to each other. The two rapidly rising flanks (right) lie practically on top of one another and the major differences in front of the gently inclined plateaus of the measured curve 41 and the simulated curve 42 have been reduced.

Figure 5:
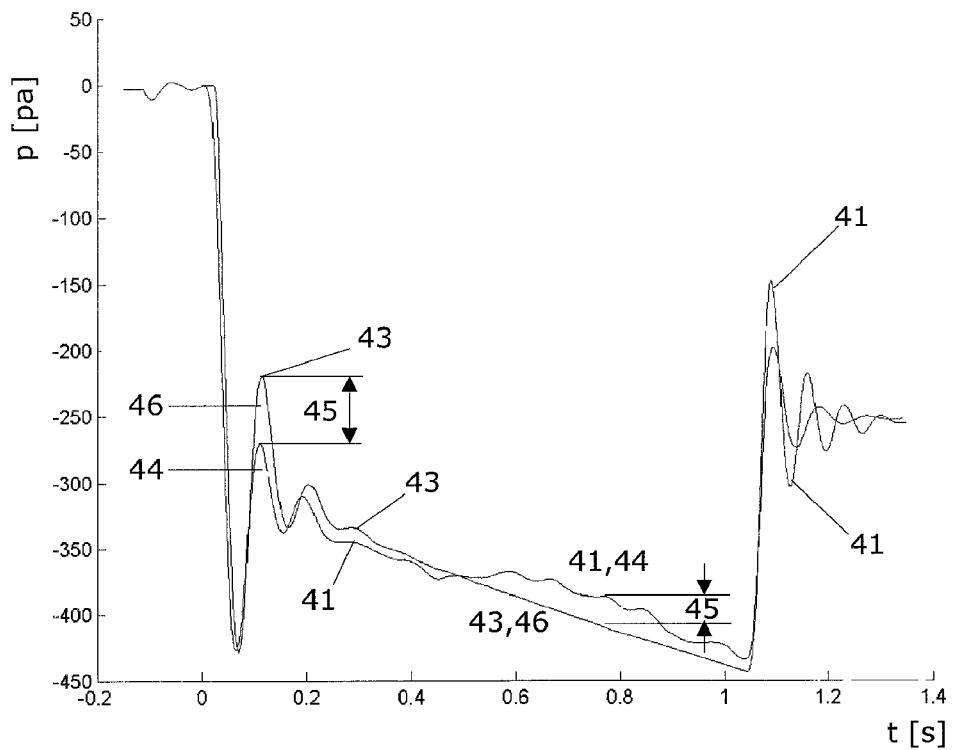
FIG. 5 Step 5, in which the attenuation behavior of the system liquid has been taken into consideration. This characteristic curve will be subsequently referred to as the iterative curve.

In FIG. 5 the two large, steep falling flanks (left) are very close and run practically parallel to each other after a fifth approximation step that takes the attenuation behavior of the system liquid into account. The two gently inclined plateaus (center) are now very close and are partially overlapping. In particular, the values before the rise of the right-hand flank now lie very close to each other. The two rapidly rising flanks (right) now lie on top of one another and the major differences at the tune point to the gently sloping plateaus have been further reduced. The simulated curve 42 obtained at this point shall subsequently be referred to as the iterative curve 43. The sections of the measured curve 44 shown here as examples are compared with the corresponding sections of the iterative curve 46, with any difference between these two sections of characteristic curve that is larger than the threshold value 45 achieved here being taken as a decision making criterion for accepting or rejecting the pipetted sample.

As mentioned previously, this procedure was performed with only four selected parameters (not shown) for sample dispensing accordingly.

As demonstrated, the simulated curves generated with this model closely match the actual measured pressure curves. However, the simulated curves do not have any signal noise whatsoever. This noise is primarily evident in the gently inclined plateaus and contributes largely to the difference between the two characteristic curves at that point. It has also been shown that the simulated curve 42 can achieve a very good match between the iterative curve 43 and the actual measured pressure curve 41 by adjusting the physical parameters using the especially developed fitting routines.

All the advantages and features in the context of measuring the pressure pattern in the fluid chamber of a pipetting apparatus in accordance with the invention apply analogously for measuring the flow in the fluid chamber of a pipetting apparatus in accordance with the invention.

3. Comparison of the Iterative Curve with the Actual Measured Curve

Based on specific differences between these two characteristic curves for aspiration or dispensing, a distinction can be made now between correctly and incorrectly pipetted samples. Preferably this involves the use of specific discriminators to qualify errors and in special cases to even quantify potential errors.

During pipetting various errors can occur that can be attributed to properties of the pipetted samples, the pipette tips and vessels used, and the pipetting apparatus employed. All these errors are manifested in the form of specific signatures or changes in the characteristic pressure or flow curves recorded. These signatures can therefore be used to detect and differentiate errors. In order for the pipetting apparatus in accordance with the invention to be as flexible as possible and to be able to be used in all possible applications, approximately 100 discriminatory parameters have already been identified. Based on entire sets of characteristic pressure or flow curves, which are representative of various pipetting applications, the most suitable parameters have been selected and implemented here in the proposed discrimination algorithm. The details of such discriminatory parameters and their combination with corresponding algorithms are known per se and are therefore not discussed here in any detail.

Preferably, the computer program product enables the processor of the pipetting apparatus to divide the iterative curve into its characteristic sections, selected from a group consisting of the inflection points, periodic cycles, frequencies, local maximums and minimums and also slopes. In addition, preferably deviations in the corresponding sections of the actual measured curve are ascertained in comparison with the defined threshold values in relation to the matching sections of the iterative curve, with pipetting being matched to one of a plurality of decision-making criteria using these deviations.

4. Possible Uses of the Model Parameters

The pipetting process depends on several parameters, including ambient conditions, sample properties, and instrument properties. At least in part, these parameters must be included in the physical model of the pipetting channel described above. Due to the nature of the physical model and that of the adjustment or fitting, the parameters used for fitting or adjusting the simulated curve to the measured curve are issued as approximation values during the course of the process by the processor of the pipetting apparatus in accordance with the invention. For this reason the result of the adjustment process can not only be used to differentiate correct pipetting characteristic curves from incorrect ones.

A pipetting apparatus in accordance with the invention, the control system of which is preferred for the purpose of activating the computer program product described here to enable it to individually accept or reject each of the pipetted liquid samples on the basis of the measured physical parameters, is disclosed in the Swiss patent application CH 01223/05 by the same applicant and the scope of the disclosure is expressly included in this patent application. This pipetting apparatus is based on pressure measurement technology and is shown schematically in FIGS. 6 to 11 in preferred, exemplary embodiments.

Figure 6:
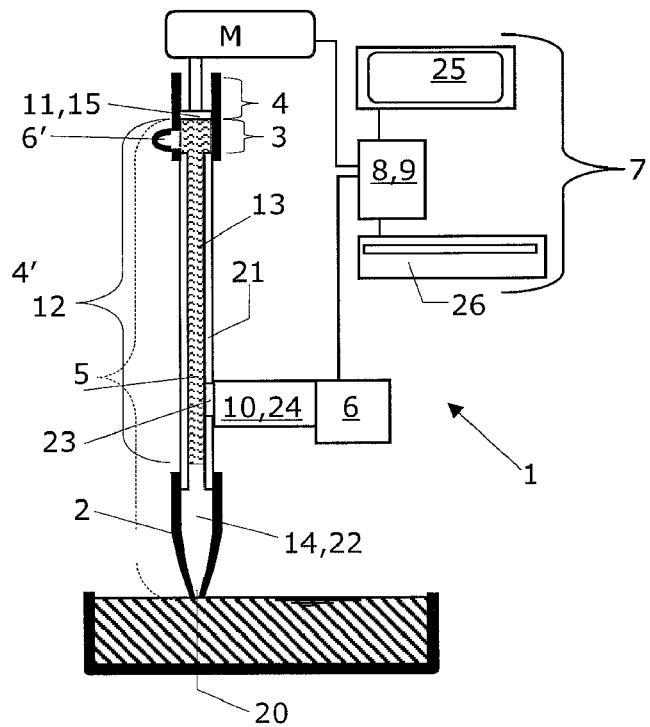
FIG. 6 a vertical section through a pipette device in accordance with the invention.

FIG. 6 shows a vertical section through a pipetting apparatus 1. This apparatus or system that is suitable for executing the method in accordance with the invention includes a plunger pump. This pump 4 is for example a "CAVRO XP3000 plus Modular Digital Pump" (Tecan Systems Inc., 2450 Zanker Road, San José, Calif. 95138, USA) or a bellows pump such as is known from U.S. Pat. No. 5,638,986. The plunger 15 is actuated by the motor M. This apparatus also comprises a known disposable pipette tip 2, fitted onto a pipe shaped pipette encompassing a fluid chamber 5. The pipette tip 2 is attached to a mounting 21. The fluid chamber 5 contains a column 12, formed by a system liquid 13. The fluid chamber 5 extends from the active parts of the pump, i.e. from the plunger 15, via a pump conduit 3 developed in accordance with the requirements of the apparatus, a system liquid column 13 and an air gap 22 to the pipette tip 2. The pump conduit ("tubing") can also include components that are not vertical. The entire removable or disposable pipette tip 2 is filled with a gas (usually air) and is slightly immersed in a liquid sample located in a container. Immersing the pipette tip 2 into the sample fluid causes the pressure to alter in the fluid chamber 5. These pressure changes also result in changes to the pressure in the measurement chamber 24 that it is pneumatically connected with the fluid chamber 5 (preferably separated by means of a flexible membrane 23), with said changes being recorded by the pressure sensor 6 and converted into measurement signals. These measurement signals are processed by the processor 8 and can be reproduced as a pressure characteristic curve 41 (cf. FIG. 1-5) on a monitor 25 or a printer 26, therefore being displayed to an operator. Preferably, the apparatus includes an additional pressure sensor 6' in the area of the pump conduit 3 that connects the pipette to the plunger pump 4 in the form of tubing. Preferably, this additional pressure sensor 6' is also connected to the processor 8 (not shown). Alternative pipette tips include the illustrated disposable tips made of inert synthetic material, e.g. inexpensive polypropylene. Steel needles (with or without for instance titanium, platinum or Teflon derivative coated tips) can also be used and are then installed preferably as permanent, non-disposable pipette tips.

Figure 7:
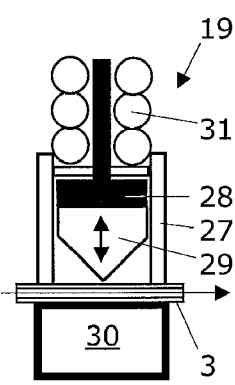
FIG. 7 a partial section through an electromechanical variant of an alternative, pump-independent pulse unit.

FIG. 7 shows a partial section through an electromechanical variation of an alternative, non-pump dependent pulse generator 19 that can also be used to generate pressure changes in the fluid chamber 5. The pump conduit extends through a cylinder 27. A plunger 28 with a wedge 29 is arranged inside this cylinder 27, with said wedge being arranged movably essentially perpendicular to and against the closed surface of the pump conduit 3. Preferably, the wedge 29 is made of soft synthetic material and/or has a rounded edge to prevent the pump conduit from being damaged. Other shapes can be selected for the wedge 29, such as balls or bodies with plane or curved surfaces. Preferably, a solid floor 30 closes off the cylinder 27 on the side opposed to the plunger 28. This movement reversibly deforms the pump conduit 3, triggering the said pulse. Single pulses and also a series of pulses can be triggered such that the liquid column is only moved briefly or is oscillated. Preferably, this pulse generator can be operated along an X, Y or Z axis independently of the movement in the pipette and of pump 4 operation. This pulse generator 19 is particularly suitable for detecting gas bubbles in the system liquid 13 in the fluid chamber 5. The actuator can be for example a coil 31.

Figure 8:
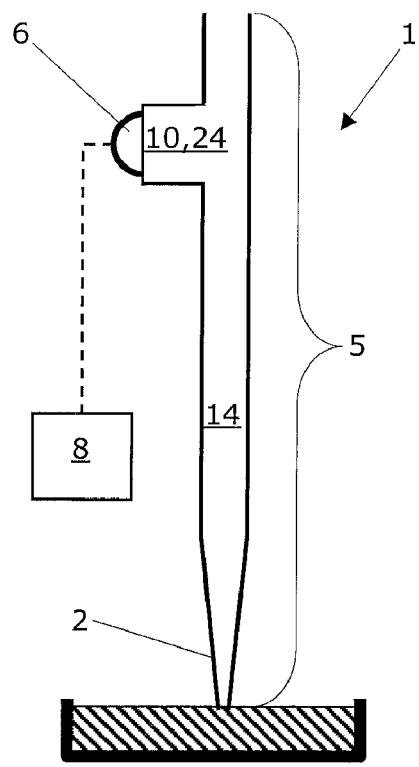
FIG. 8 a vertical section through a device or system suitable for executing the method in accordance with the invention in accordance with a first embodiment and in accordance with a first application.

FIG. 8 shows a vertical section through a device or system suitable for executing the method in accordance with the invention in accordance with a first embodiment and in accordance with a first application; This apparatus comprises a fluid chamber 5 that is connected to a measurement chamber 24. This connection is developed here as a direct, open passage between the two chambers 5,24. The internal pressure of the measurement chamber 24 is monitored by a measurement probe 6 developed as a pressure sensor, connected to a processor 8. In an alternative embodiment, the pressure sensor 6 could be connected directly to the fluid chamber 5 (not shown). The entire fluid chamber 5 of the pipette or pipette tip 2 is filled with a gas 14 in this case. The pipette tip 2 touches the surface of a fluid that is presented as a sample in a container. Such containers can be of any shape and have any content and are developed for instance as sample tubes, microplate wells, troughs or Petri dishes. When the tip of the pipette is immersed in the sample fluid the gas column 14 in the fluid chamber 5 is subject to pressure changes or pressure fluctuations.

Figure 9:
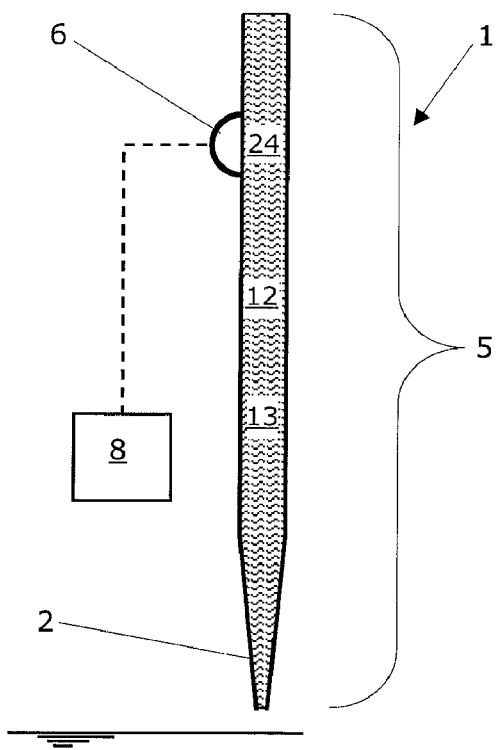
FIG. 9 a vertical section through a device or system suitable for executing the method in accordance with the invention in accordance with a second embodiment and in accordance with a second application.

FIG. 9 shows a vertical section through a device or system suitable for executing the method in accordance with the invention in accordance with a second embodiment and in accordance with a second application. This apparatus comprises a fluid chamber 5 that is connected to a measurement chamber 24. The fluid chamber 5 in this case actually also forms the measurement chamber 24. The internal pressure of the measurement chamber 24 is monitored by a measurement probe 6 developed as a pressure sensor that is connected to a processor 8. Alternatively, the measurement probe 6 can be developed as a flow sensor to detect and measure the flow of the system liquid 13 in the fluid chamber 5. The fluid chamber 5 of a pipette or a pipette tip 2 touches the surface of a fluid. When the pipette tip is immersed in the fluid, the system liquid column 13 in the fluid chamber 5 is subject to pressure changes or pressure fluctuations.

Figure 10:
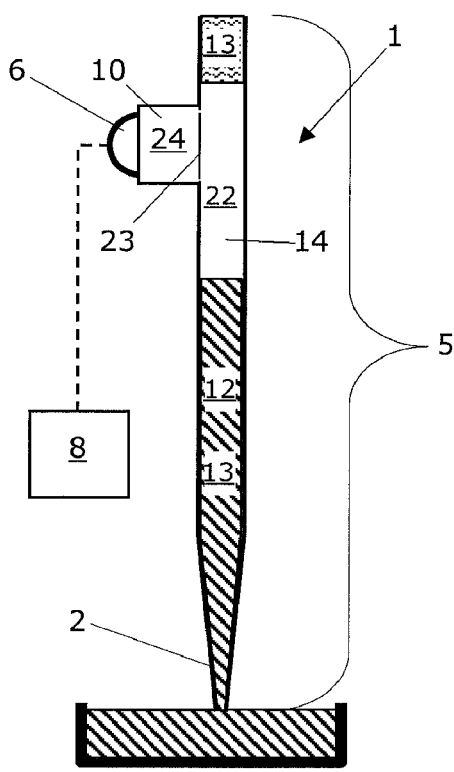
FIG. 10 a vertical section through a device or system suitable for executing the method in accordance with the invention in accordance with a third embodiment and in accordance with a third application.

FIG. 10 shows a vertical section through a device or system suitable for executing the method in accordance with the invention in accordance with a third embodiment and in accordance with a third application. This apparatus comprises a fluid chamber 5 that is connected to a measurement chamber 24. This connection is developed here as a flexible sealing membrane 23 arranged between the two chambers 5,24. The internal pressure of the measurement chamber 24 is monitored by a pressure sensor 6 connected to a processor 8. A first section of the fluid chamber, which in this case only comprises the rear section of the fluid chamber 5 of a pipette or pipette tip 2, is filled here with an air gap 22 and a system liquid 13. The system liquid 13 can also be dispensed with here. Preferably, the air gap 22 is arranged in the region of the measurement chamber 24, especially in the first embodiment (cf. FIG. 8), in which this connection is developed as a direct, open passage between the two chambers 5,24. However, in this present embodiment it is not necessary as the membrane 23 protects the measurement chamber 24 from impinging sample or system liquid. The pipette tip 2 is slightly immersed in the fluid and sample fluid has already been drawn into the pipette tip 2. When sample fluid is drawn up or aspirated, the column of fluid (in this case comprising sample fluid, a gas 14 and eventually system liquid 13) in the fluid chamber 5 is subject to pressure changes and pressure fluctuations.

Figure 11:
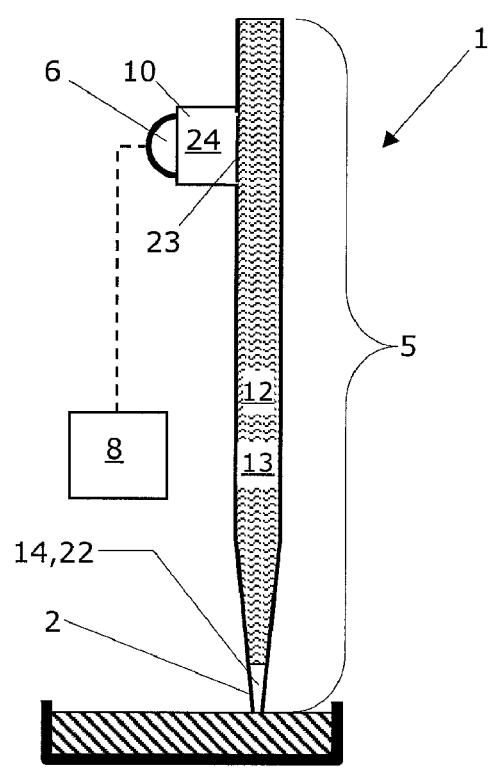
FIG. 11 a vertical section through a device or system suitable for executing the method in accordance with the invention in accordance with a third embodiment and in accordance with a fourth application.

FIG. 11 shows a vertical section through a device or system suitable for executing the method in accordance with the invention in accordance with a third embodiment and in accordance with a fourth application. This apparatus is developed in the same manner as that shown in FIG. 10. The entire fluid chamber 5 of a pipette or pipette tip 2 is filled in this case in the region of the tip with an air gap 22 and otherwise with system liquid 13. In the present embodiment the membrane 23 protects the measurement chamber 24 from impinging system liquid 13. The pipette tip 2 is dipped slightly into the fluid. When the sample fluid is drawn up, the fluid column in the fluid chamber 5, in this case comprising a gas 14 and system liquid 13, is subject to pressure changes or pressure fluctuations.

Departing from the illustrated plunger pumps 4, where the motion source 11 is the plunger 15, the pipetting apparatus 1 in accordance with the invention can also be equipped with a micropump comprising a membrane 16 and/or an actuator 17 (not shown), developed in this case as the motion source 11. Appropriate micropumps have long been known and are for instance described in EP 1 142 624 A2 or U.S. Pat. No. 6,179,584 B1. Another alternative motion source 11 that can be employed is the gear wheel 18 of a gear wheel pump (not shown) as for instance described in DE 1 703 406 A1. Other pumps, such as for instance widely known peristaltic pumps, can also be used to transport the system liquid.

Major characteristics and advantages of the present intervention include:

The computer program product that can be activated in the pipetting apparatus in accordance with the invention is based on an—actually counterintuitive—approach or method to simulate a characteristic curve by employing a physical model and taking practical know-how into account, approximating this curve to an actual measured curve, and then comparing said curve with this measured curve by:

using a mathematical model to calculate a simulated curve, taking all essential parameters into consideration;

approximating the simulated curve to the actual measured curve to obtain an iterative curve, with the modifiable parameters (such as e.g. sample viscosity, surface tension, sample fluid density, and pipette tip geometry) being modified systematically;

comparing the actual measured curve with the iterative curve, analyzing the elements specific to the characteristic curves (such as e.g. slopes, maximums, zero crossovers);

classifying each individual pipetted sample on the basis of this comparison of the measured curve with the iterative curve, with specific criteria, such as for instance the proportion of the deficient volume serving as the basis, and matching this classification of a pipetted sample to the corresponding sample.

The pipetting apparatus in accordance with the invention preferably comprises a computer program product, which can be adapted at three levels to specific applications:

differentiation of parameters (strictness), where strictness defines the range of tolerance between a section of the iterative curve 46 and the corresponding section of the measured curve 44. Discriminatory characteristics of these curves (cf. FIG. 5) comprise differences in overshooting, slope, inflection points, local maximums and minimums, and intersecting plateaus 41,43;

the exchange or combination of around 100 differentiation characteristics at present programmed as a so-called "plug-in";

the exchange of the physical model.

The pipetting apparatus in accordance with the invention permits errors to be monitored not only very specifically, but also very sensitively: The measurement of the tolerable changes in characteristic pressure curves or flow patterns in the pipetting apparatus in accordance with the invention allows the positive measurement of pipetted volumes with a negligible volume deficit and the differentiation of such volumes with an intolerable volume deficiency.

Large clots that can block the pipette tip permanently can be distinguished from one or a plurality of smaller clots which are drawn into the pipette tip only after a certain additional negative pressure has been reached in the pipette tip.

LIST OF DRAWING REFERENCES

1 Pipette apparatus
2 Pipette tip
3 Pump conduit
4 Pump
5 Fluid chamber
6 Measurement probe
7 Device control system
8 Processor
9 Data storage device
10 Fluid-filled chamber
11 Motion source
12 Column
13 System liquid
14 Gas, gas column
15 Plunger
16 Membrane
17 Actuator
18 Gearwheel
19 Pulse generator
20 Pipette tip outlet
21 Mounting
22 Air gap
23 Flexible membrane
24 Measurement chamber
25 Monitor
26 Printer
27 Cylinder
28 Plunger
29 Wedge
30 Solid floor
31 Coil
32
33
34
35
36
37
38
39
40
41 Measured curve
42 Simulated curve
43 Iterative curve
44 Sections of measured curve
45 Threshold values
46 Sections of iterative curve

We claim:

1. A method for accepting and rejecting a sample pipetted by a pipetting apparatus, comprising the following steps:
   a) providing a pipetting apparatus comprising:
      a pipette tip for aspirating and dispensing a liquid sample,
      a pump, connected to the pipette tip by a pump conduit, for generating negative pressure or positive pressure in the pipette tip,
      a fluid chamber defined by the pipette tip and/or the pump conduit,
      a pressure sensor functionally connected to the fluid chamber for measuring pressure changes in this fluid chamber during a pipetting process, and
      a device control system with a processor and an activatable computer program product, which, when activated, enables the control system to individually accept or reject pipetted liquid samples on the basis of the pressure changes measured;
   b) providing model parameters selected from a group comprising properties of liquid samples and instrument properties of the pipetting apparatus for generating a simulated curve using a mathematical model, wherein said model parameters are stored by the processor and are selectable and modifyable,
   c) selecting at least one model parameter from the group comprising:
      volume of fluid to be pipetted, and
      type of the pipette tip to be used,
      and entering the selected model parameter(s) in the processor:
   d) generating a simulated curve for a pipetting process by the activated computer program product using a mathematical model, said simulated curve simulating a pressure characteristic curve for a pipetting process as recordable by the pressure sensor, wherein the simulated curve is generated based on the model parameters as stored in the processor;
   e) storing the simulated curve by the processor;
   f) pipetting a liquid sample with the pipetting apparatus;
   g) measuring the pressure changes in the fluid chamber during the pipetting process using the pressure sensor;
   h) generating an actual measured pressure curve of the pipetting process by the processor;
   i) approximating the simulated curve to the actual measured pressure curve by systematically selecting and varying modifyable model parameters using the computer program product, thereby generating an iterative curve, wherein tolerance ranges for the model parameters are defined, within which these model parameters may vary;
   j) comparing the iterative curve with the actual measured pressure curve using the activated computer program product by analyzing deviating sections within the actual measured pressure curve that deviate from respective sections of the iterative curve; and
   k) accepting or rejecting the pipetting process based on the deviations in view of defined threshold values using the activated computer program product and the processor of the device control system, and thereby accepting or rejecting the pipetted liquid sample.

2. Method according to claim 1, wherein at least one further model parameter is selected from a group comprising:
   at least one fluid class, wherein a fluid class consists of instrument parameters defined for pipetting a liquid sample, and
   the diameter of the pipette tip outlet and the wettability of the pipette tip.

3. Method according to claim 2, wherein the set of parameters for a fluid class consists of variables selected from a group comprising:
- type, ramp parameters and delivery parameters of the pump used,
- use and volume of an air gap, and
- insertion and withdrawal speed of the pipette tip, immersion depth of the pipette tip, and acceleration and deceleration ramps of pipette tip movements.

4. Method according to claim 1, wherein at least one further model parameter is selected from a group comprising:
- viscosity and density of a sample liquid.

5. Method according to claim 1, wherein when comparing the iterative curve with the actual measured curve, the method comprises the following step:
- dividing the iterative curve into characteristic sections using the processor, wherein the characteristic sections are selected from a group consisting of the inflection points, periodic cycles, frequencies, local maximums and minimums and also slopes.

6. A method for accepting and rejecting a sample pipetted by a pipetting apparatus, comprising the following steps:
a) providing a pipetting apparatus comprising:
- a pipette tip for aspirating and dispensing a liquid sample,
- a pump, connected to the pipette tip by a pump conduit, for generating negative pressure or positive pressure in the pipette tip,
- a fluid chamber defined by the pipette tip and/or the pump conduit,
- a flow meter functionally connected to the fluid chamber for measuring flow changes in this fluid chamber during a pipetting process, and
- a device control system with a processor and an activatable computer program product, which, when activated, enables the control system to individually accept or reject pipetted liquid samples on the basis of the flow changes measured;

b) providing model parameters selected from a group comprising properties of liquid samples and instrument properties of the pipetting apparatus for generating a simulated curve using a mathematical model, wherein said model parameters are stored by the processor and are selectable and modifyable, c) selecting at least one model parameter from the group comprising:
- volume of fluid to be pipetted, and
- type of the pipette tip to be used,
and entering the selected model parameter(s) in the processor;

d) generating a simulated curve for a pipetting process by the activated computer program product using a mathematical model, said simulated curve simulating a flow characteristic curve for a pipetting process as recordable by the flow meter, wherein the simulated curve is generated based on the model parameters as stored in the processor;

e) storing the simulated curve by the processor;

f) pipetting a liquid sample with the pipetting apparatus;

h) measuring the flow changes in the fluid chamber during the pipetting process using the flow meter;

h) generating an actual measured flow curve of the pipetting process by the processor;

i) approximating the simulated curve to the actual measured flow curve by systematically selecting and varying modifyable model parameters using the computer program product, thereby generating an iterative curve, wherein tolerance ranges for the model parameters are defined, within which these model parameters may vary;

j) comparing the iterative curve with the actual measured flow curve using the activated computer program product by analyzing deviating sections within the actual measured flow curve that deviate from respective sections of the iterative curve; and k) accepting or rejecting the pipetting process based on the deviations in view of defined threshold values using the activated computer program product and the processor of the device control system, and thereby accepting or rejecting the pipetted liquid sample.

7. Method according to claim 6, wherein at least one further model parameter is selected from a group comprising:
- at least one fluid class, wherein a fluid class consists of instrument parameters defined for pipetting a liquid sample, and
- the diameter of the pipette tip outlet and the wettability of the pipette tip.

8. Method according to claim 7, wherein the set of parameters for a fluid class consists of variables selected from a group comprising:
- type, ramp parameters and delivery parameters of the pump used,
- use and volume of an air gap, and
- insertion and withdrawal speed of the pipette tip, immersion depth of the pipette tip, and acceleration and deceleration ramps of pipette tip movements.

9. Method according to claim 6, wherein at least one further model parameter is selected from a group comprising:
- viscosity and density of a sample liquid.

10. Method according to claim 6, wherein when comparing the iterative curve with the actual measured curve, the method comprises the following step:
- dividing the iterative curve into characteristic sections using the processor, wherein the characteristic sections are selected from a group consisting of the inflection points, periodic cycles, frequencies, local maximums and minimums and also slopes.

* * * * *